Figure 3:
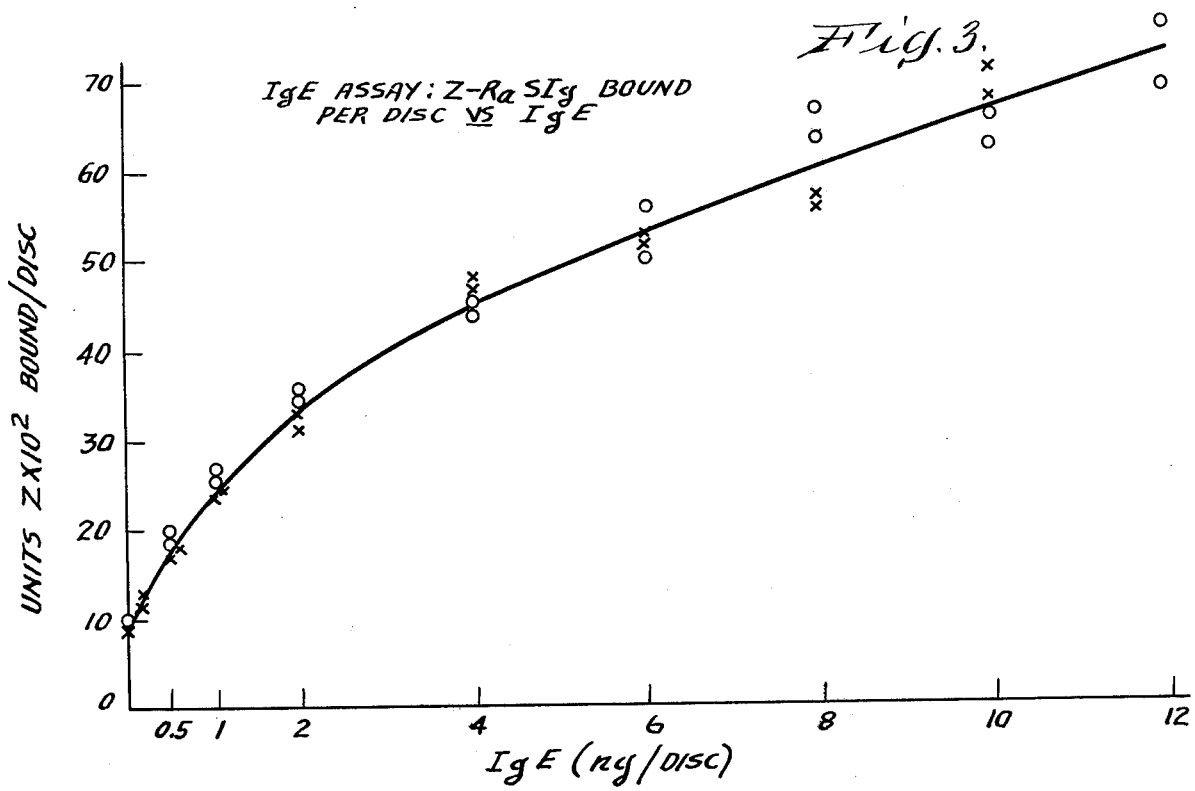

United States Patent [19]
Weltman et al.

[11] 4,002,532
[45] Jan. 11, 1977

[54] ENZYME CONJUGATES

[76] Inventors: Joel K. Weltman, 4 Wildacre Lane, Barrington, R.I. 02806; M. Boris Rotman, 11 Mayflower St., Providence, R.I. 02906

[22] Filed: Oct. 21, 1974

[21] Appl. No.: 516,331

[52] U.S. Cl. .................... 195/103.5 A; 195/63; 195/68; 195/DIG. 11; 195/103.5 R; 260/112 R; 424/12
[51] Int. Cl.² .................... G01N 31/14; C07G 7/02
[58] Field of Search ............. 195/63, 68, DIG. 11, 195/103.5 R, 103.54; 260/112 R; 424/12

[56] References Cited

UNITED STATES PATENTS

| | | | |
|---|---|---|---|
| 3,639,558 | 2/1972 | Csizmas et al. | 195/63 X |
| 3,654,090 | 4/1972 | Schuurs et al. | 195/103.5 R |
| 3,839,153 | 10/1974 | Schuurs et al. | 195/63 X |
| 3,859,169 | 1/1975 | O'Driscoll et al. | 195/63 |

OTHER PUBLICATIONS

Arrameas et al., Biologically Active Water–Insoluble Protein Polymers, J. of Biol. Chem., vol. 242, No. 7, 1967, (pp. 1651-1659).

*Primary Examiner*—David M. Naff

[57] ABSTRACT

This invention relates to the provision of enzyme-macromolecule conjugates by conjugation with polyfunctional reagents in the presence of organic compounds which act as conditioners. Conjugation of enzymes with antibodies in the presence of conditioner yields conjugates with increased immunological specificity. Organic polyamines of either high or low molecular weight are conditioners. Conditioners are especially useful for conjugation of polymeric and unstable enzymes such as $\beta$-D-galactosidase. The high degree of immunospecificity and sensitivity achieved with conditioners yields conjugates suitable for detection and quantification of substances, such as IgE, in nanogram quantities in biological fluids with many interfering substances.

16 Claims, 4 Drawing Figures

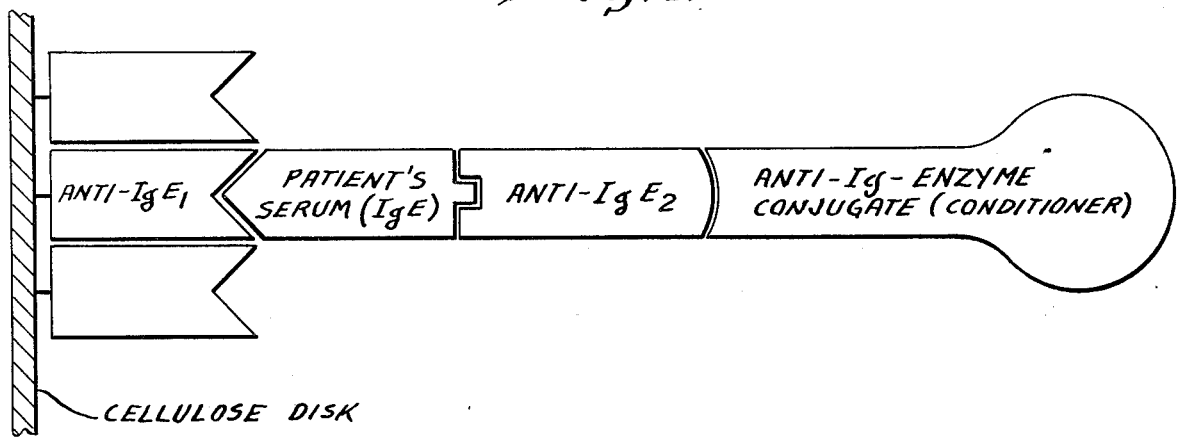
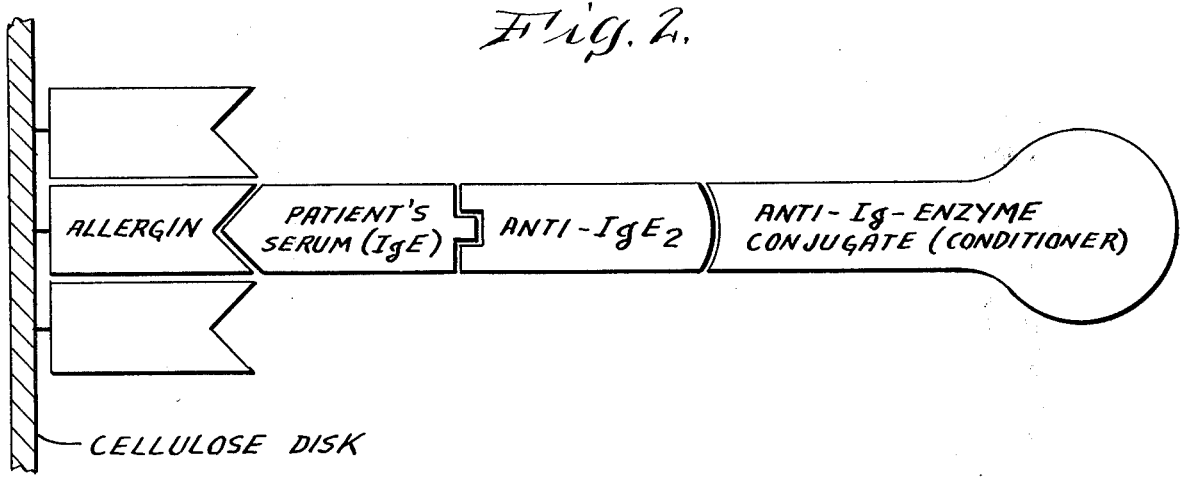

ENZYME CONJUGATES

Covalent conjugates of enzymes are used for detection of antigens, antibodies, allergens, hormones and other macromolecules because of the ease, sensitivity and specificity of enzyme assays. For example, enzymeantibody conjugates absorbed onto solid specimens make possible the sensitive histochemical detection of specific antigens (See U.S. Pat. No. 3,654,090 and J. S. Ram et al., Fed. Proc. (1966) 25, 732). Covalent conjugates of enzymes with other macromolecules are prepared with polyfunctional, frequently with bifunctional, coupling reagents. Such coupling reagents are characterized by at least two reactive groups. Typical coupling reagents are diisocyanates, carbodiimides, p,p'-di-fluoro-m,m'-dinitrodiphenylsulfone, glutaraldehyde, dimethyladipimate, formaldehyde, bisdiazobenzidine and aromatic halide disulfonates. Coupling reagents link reactant pairs by intermolecular reaction with one or more types of substituent groups in the reactants, such as $-NH_2$, $-COOH$, $-SH$, phenolate, or imidazol. Unfortunately, in many cases serious problems are encountered in the use of coupling reagents to synthesize enzyme conjugates. These problems include: inactivation of either the enzyme or the coupling partner, such as an antibody, to which the enzyme is coupled; precipitation or aggregation of the conjugate; and nonspecific binding of conjugates to immunosorbents. In tests involving separations of a solid and a liquid phase, nonspecific binding of enzyme conjugates to the solid phase greatly reduces both the sensitivity and the specificity by increasing blank or background values i.e., "background noise". Preservation of sensitivity and specificity is essential for the determination of substances present in nanogram quantities in biological fluids, such as serum or urine, which contain a large number of interfering substances.

It is an object of this invention to provide new conjugates of enzymes and other macromolecules with polyfunctional reagents.

It is a further object of this invention to provide a method of coupling enzymes with other macromolecules in a manner which substantially avoids the inactivation of either the enzyme or the coupling partner such as an antibody to which the enzyme is coupled; precipitation or aggregation of the conjugate; and nonspecific binding of the conjugate to solid absorbents.

It is still a further object of this invention to provide sensitive and specific techniques for the detection of macromolecules present in small quantities in biological fluids which contain a large number of interfering substances.

In accordance with one aspect of this invention there is provided a new method for coupling enzymes to macromolecules. The basis of the method is the unexpected finding that some substances act as "conditioners" during coupling reactions with polyfunctional reagents. Conditioners are chemical compounds which, if used during conjugation reactions of enzymes and macromolecules with polyfunctional reagents, have the following effects:

i. substantial elimination of precipitation of enzyme conjugates;
ii. reduction of non-specific adsorption of enzyme conjugates to solid phase immunosorbents;
iii. preservation of enzyme activity of the conjugates;
iv. preservation of the specific binding properties of the conjugated partner or partners;
v. resistance of the enzyme activity of the conjugates to denaturants, such as detergents, urea and salts.

The conjugates of this invention are the products of enzymes and other biological macromolecules coupled with a polyfunctional coupling agent in the presence of a polyamine conditioner.

The biological macromolecules can be nucleic acids, proteins, glycoproteins or lipoproteins, all of which contain amino groups. Examples of such macromolecules are deoxy and ribonucleic acids, viral proteins, allergens, immunoglobulins, blood group substances, transplantation antigens, carcino embryonic antigen, $\alpha$-fetoprotein and other tumor specific antigens, growth hormone and other polypeptide hormones.

Any enzyme can be used to form the conjugates of this invention. Particularly useful are enzymes which can be detected either chromogenically or fluorogenically with great sensitivity. Among the useful enzymes there can be named acid and alkaline phosphatases, alcohol dehydrogenase catalase, glucose and galactose oxidases, $\alpha$ and $\beta$-galactosidases, lactate dehydrogenase, lysozyme, luciferase, peroxidases, ribonuclease, rodhanase and esterases.

Coupling agents for use in forming conjugates of the present invention are known materials which have been previously used to form conjugates. Typical coupling agents are polyfunctional, most often bifunctional, reagents with active hydrogen, halogen, aldehyde, sulfonate or ester groups capable of reacting with one or more types of substituent groups in the macromolecule reactants such as $-NH_2$, $-COOH$, $-SH$, phenolate or imidazol. Such compounds are typified by the bifunctional reagents named above.

We found that organic polyamines of either high or low molecular weight are conditioners. For example, macromolecules with multiple amino groups, i.e., 2, 3, 4, etc. amino groups, such as synthetic polypeptides or natural proteins are conditioners. The conditioner must be different from either of the coupling partners used in the formation of the conjugate so that it will not have an adverse effect on the assay of the conjugate. Diaminodipropylamine is an example of a low molecular weight conditioner. Other low molecular weight conditioners may be aromatic amines such as phenylenediamine, 4.4'-diaminobenzophenone, p,p'-diaminodiphenyl methane naphthalene diamine, benzidine, 2,6-diaminopurine, or the series of aliphatic diamines, such as, ethylene diamine, propylene diamine or hexamethylene diamine.

The conditioner should be free of groups which may react with the amine such as reactive acyl, including carboxy keto acrylhalide, aldehyde groups, sulfonic acid groups and, in general, any other groups which react in accordance with known principles with the amino groups of the conditioner to block said amino groups. However, any other substituents may be present on the conditioner molecule, e.g. alkyl, aryl, alkoxy, nitro, mercapto, and peptidyl.

The discovery of conditioners enabled us to prepare useful antibody conjugates of $\alpha$-D-galactosidase, a bacterial enzyme which had been thought previously to be unsuitable for use in enzyme-antibody conjugates (Hermann and Morse, Immunochem. (1974), 11, 79–82). Conjugates of $\alpha$-D-galactosidase are desirable because of the characteristics of this enzyme, namely, sensitivity of assay and availability of stable chromogenic and fluorogenic substrates. Assays for this enzyme have been developed which are more sensitive than those for any other enzyme, i.e., a single molecule of β-D-galactosidase can be detected. The drawbacks previously observed with β-D-galactosidase conjugates of antibodies are loss of antibody activity in the conjugate and instability of the enzyme in the presence of detergents, urea and certain cations. The instability of β-D-galactosidase is likely due to the tetrameric structure of the enzyme. This invention has overcome these drawbacks and provides the additional advantageous properties mentioned in items i, ii, iii, iv and v above.

The use of conditioners to improve the properties of conjugates should find application in many tests involving enzyme conjugates. For example, conditioners may be used by those skilled in the art to produce improved reagents for detection of macromolecules such as allergens, serum proteins, hormones, antigens characteristic of bacteria, viruses, fungi, protozoa and helminths and for histocompatibility typing. For convenience and by way of example we will illustrate application of β-D-galactosidase-anti-IgE conjugates produced with conditioners for detection and quantification of total and allergen specific human IgE antibodies. Antibodies of the IgE class are directly implicated in common allergic diseases such as asthma and hay fever. Antibodies of the IgE class comprise only about 0.005% of the total antibodies in human blood; accordingly, detection of IgE is difficult because of the presence of similar proteins in the serum. Until recently, the only tests for IgE antibodies were in vivo assays such as those involving skin testing or bronchial provocation. These in vivo tests subject patients to inconvenience and are fraught with risks. It is, therefore, of great importance and interest that antibodies of the IgE class be readily detected and quantified in vitro so that specific allergies can be identified and appropriate therapy instituted.

All currently available commercial in vitro tests for IgE antibodies have serious limitations and drawbacks which are circumvented by conditioned conjugates of β-D-galactosidase with anti-IgE. One of the drawbacks is the use of expensive, unstable, radioactive reagents, because these reagents require laboratories well equipped for handling and detecting radioactivity. Thus, radioactive reagents place the tests outside the realm of feasibility of the average medical clinic. Furthermore, the instability of the radioactive reagents shortens the shelf-life of the test and adds to the costs. The second serious drawback of current tests is that they all require relatively large amounts of IgE; IgE is an extremely rare and valuable protein since it has been obtained from only four suitable human donor patients. The requirement for large amounts of IgE is the result of either consumption of IgE in each test performed or from production of immuno-specific reagents.

The enzyme for preparation of conjugates by means of this invention can be obtained by adaptation of prior art techniques such as the method of Craven et al. (J. Biol. Chem. (1965) 240, 2468). In this invention a buffered mixture of the enzyme, the coupling agent, and the conditioner is prepared. The mixture should contain the components in the following appropriate proportions.

| | Range |
|---|---|
| ENZYME | $3 \times 10^{-7} M - 3 \times 10^{-5} M$ |
| CONDITIONER | $5 \times 10^{-4} M - 5 \times 10^{-2} M$ |

-continued

| | Range |
|---|---|
| COUPLING AGENT | $5 \times 10^{-4} M - 5 \times 10^{-2} M$ |

The mixture is allowed to react at room temperature and then the other biological macromolecular material, e.g. an antibody, is added. The proportion of macromolecular material to enzyme can be in the range of 0.1 to 5.0. Reaction conditions are maintained for an additional 0.5 to 24 hours and then the reaction is stopped by dialysis, gel filtration or addition of $NaHSO_3$. The conjugate can then be isolated by conventional purification techniques. By using a conditioner as required by this invention, the resultant conguate retains substantially all of the initial enzyme activity, in contrast to the conjugates prepared without conditioner which lose substantially all of the initial enzyme activity.

The manner in which the enzyme-antibody conjugates produced by cross-linking in the presence of conditioner are used detect and quantify total IgE antibodies is diagrammatically represented in FIG. 1. As shown in FIG. 1, antibodies to human IgE (Anti-IgE$_1$) are insolubilized to form an immunoadsorbent. This insolubilization may be achieved by the use of many well known coupling reagents and the solid support may be of a variety of materials such as kaolin, charcoal, red blood stroma cellulose and cellulose derivatives, glass, polystyrene, latex and polyurethane (Silman and Katchalski, Ann. Rev. Biochem. (1966), 35, 873–908). The same methods may be applied for insolubilization of antibodies other than anti-IgE as well as for antigens and macromolecules in general. For instance, human γ-globulin has been insolubilized onto cellulose in order to measure specific antibodies against this globulin (Talmage et al., J. Inf. Diseases (1954), 94, 199). The immunoadsorbent in our experiments was either disks or erythrocytes, although many other physical and chemical forms may also be suitable such as beads, rings, microcrystals, particles and test tubes.

In the assay diagrammed in FIG. 1, the patient's serum is incubated with an Anti-IgE$_1$ disk in order to bind IgE. Subsequent to the incubation with the serum, the disk is washed several times with a buffer-detergent solvent system, to remove non-specifically adsorbed serum proteins. Following the wash, antibodies against human IgE (Anti-IgE$_2$), obtained from a species different from that used to prepare Anti-IgE$_1$ are added to the disk. The disk is again well washed to remove non-specifically adsorbed material. Anti-immunoglobulin (Anti-Ig-Enzyme) conjugated to enzyme is added; the disk is incubated and the excess enzyme conjugate is washed away. Finally, the disk is assayed for enzymatic activity. The amount of enzyme bound to the disk is a measure of the patient's IgE. Since the enzyme may be detected by either colorimetric or fluorometric techniques, the amount of IgE may be quantified without radioactive reagents. The sensitivity obtained by this method matches or surpasses that obtainable by radioimmune assay. The specificity of our method for total IgE antibodies is also high because of the use of Anti-IgE$_1$ and Anti-IgE$_2$ which form what may be called a "double-trap" sandwich. The double-trap consists of two specific anti-IgE antibodies, each obtained from a different animal species and thus, each reacting with different determinants on the IgE. The purpose of the Anti-IgE$_1$ is to trap the patient's IgE onto the immunoabsorbent while the Anti-IgE$_2$ adsorbs to the bound IgE, thereby providing specific binding sites for the Anti-Ig enzyme conjugate.

For measurement of IgE antibodies against specific allergens the procedure shown in FIG. 2 is used. As shown in FIG. 2, in the case of quantification of specific IgE antibodies, an allergin is attached to the cellulose disk. Commonly encountered allergins may be extracted from weeds, grasses, trees, animal dander, house dust and parasites. Our method requires the sequential addition of reagents and patient's serum as indicated in the diagram (from left to right) with washing of the disk with buffer-detergent solvent system between additions. As in the method for total IgE, the bound IgE is quantified by an enzymatic assay.

EXAMPLE 1

Immunospecific Detection of Insolubilized Sheep Immunoglobulin

Rabbit antibodies against sheet immunoglobulin were conjugated to $\beta$-D-galactosidase (Z) in the presence of a conditioner. To this end, rabbits were immunized by subcutaneous injections of one mg purified sheep immunoglobulin dispersed in complete Freund's adjuvant. After the immunizing schedule, immunospecifically purified antibodies against sheep immunoglobulin (RaShIg) were isolated from the rabbit serum by affinity chromatography (Williams and Chase Methods in Immunology and Immunochemistry (1967), vol. I, p. 365–384). The purified RaShIg was conjugated to Z that either was purchased from commercial sources or was prepared by the method of Craven et al. (J. Biol. Chem. (1965), 240, 2468). In order to achieve the conjugation, a mixture was prepared in phosphate buffered saline (PBS) pH 7.6 containing $6\times10^{-6}$M Z, $2\times10^{-2}$M glutaraldehyde and the conditioner, 3,3'-diaminodipropylamine, at $1.3\times10^{-2}$M. This mixture was permitted to react for 30 minutes at room temperature, following which the RaSHIg was added to a final concentration of $9\times10^{-6}$M, and the reaction was allowed to proceed for an additional 45 minutes; NaHSO$_3$ at a final concentration $2\times10^{-2}$M was then added to stop the reaction. The conjugation mixture was diluted 14 fold with PBS and then dialyzed against PBS. The dialyzed solution was clarified by filtration through a 0.45 $\mu$ Millipore membrane. This procedure produced significantly less insoluble protein than similar reactions in which conditioners were omitted. For instance, without conditioner only 2% of the initial enzymatic activity remained in solution, the other 98% being either insolubilized or inactivated. The conjugates made by the procedure described above (RaShIg-Z) contained 97% of the initial Z activity in soluble form.

The prepared RaShIg-Z conjugates were diluted in buffer E so that the solution contained 10000 units of enzyme activity per ml. The composition of buffer E was 0.14 M NaCl, 0.075M Na-PO$_4$, 1% Tween 20, 1% BSA and 0.05% NaN$_3$ Various amounts of this RaShIg-Z solution were incubated overnight with cellulose disks onto which either sheep immunoglobulin (ShIg) or Rabbit immunoglobulin (RIg) had been insolubilized. The disks were washed five times with buffer E without BSA and then placed in a solution of chromogenic substrate for the assay of Z activity. The enzyme was quantified from the rate of hydrolysis of the substrate, o-nitrophenyl-$\beta$-D-galactopyranoside, signaled by the appearance of yellow color in the solution. The amount of RaShIg-Z activity immunospecifically bound to ShIg and nonspecifically bound to RIg is given in Table I. Between 65 and 174 times more Z activity was bound to ShIg, the specific antigen, than to the irrelevant protein, RIg. Thus, conjugates prepared as described with conditioners exhibited high degree of specificity as shown by the S/N ratios in Table I. Conjugates prepared without conditioners were found to be significantly less specific, with S/N ratio of almost half of those shown in Table I.

Table I

Antibody Specificity of a Rabbit Anti-Sheep Immunoglobulin Conjugate of $\beta$-D-Galactosidase

| Enzyme Units Total Enzyme Units Added (T) | Enzyme Units Bound to Sheep Immunoglobulin Disk (S) | Bound to Rabbit Ig Disk (N) | S/N |
| --- | --- | --- | --- |
| 45 | 1.5 | 0.017 | 89 |
| 220 | 5.2 | 0.030 | 174 |
| 450 | 9.9 | 0.069 | 144 |
| 2200 | 15.0 | 0.230 | 65 |

EXAMPLE 2

Determination of Total IgE in Human Serum

Sera from rabbits and sheep immunized with human IgE myelona myeloma were obtained from commercial sources or prepared in our laboratory. The immunoglobulin fraction of the rabbit anti-IgE serum (RaIgE) was partially purified by precipitation with 40 percent (NH$_4$)$_2$SO$_4$ and insolubilized on cellulose discs. Samples to be tested for IgE were diluted in buffer E and then added to the disks. After 16 hours incubation at room temperature, the disks were washed 5 times with 2 ml of the same buffer without BSA. A 0.1ml volume of diluted sheep anti-serum against human IgE was then added to each disk and incubation at room temperature was continued for 16 hours. The disks were washed 5 times with the same buffer and 220 enzyme units of rabbit anti-sheep immunoglobulin conjugated to $\beta$-D-galactosidase (RaShIg-Z, prepared according to Example 1) were added to each disk. After 16 hours, the disks were washed 5 times and assayed for $\beta$-D-galactosidase as described for Example 1.

FIG. 3 shows a calibration curve for enzyme bound to disks as a function of human IgE added. The enzyme activity per disk increases with the IgE added to each disk. The standard error of each point is less than 5%.

Figure 4:
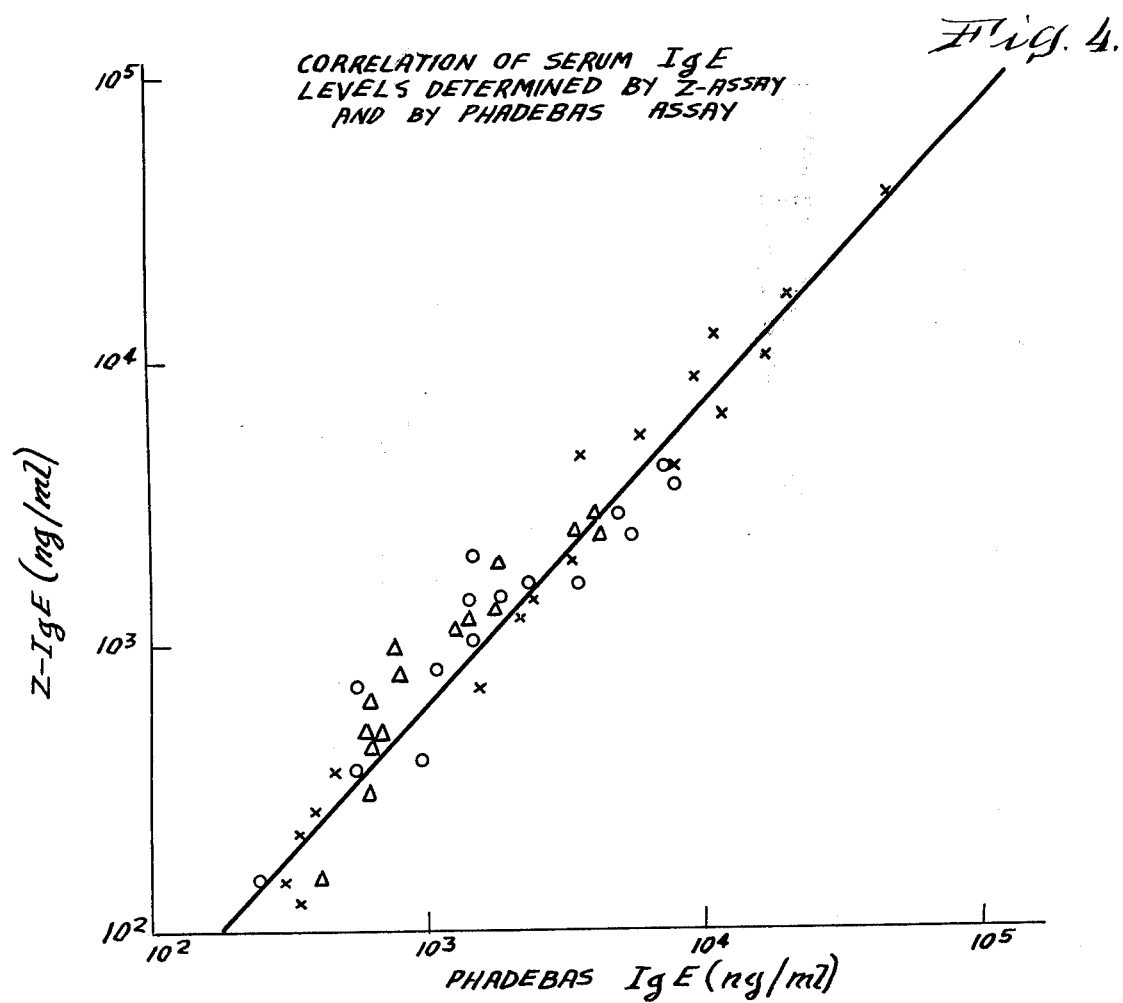

The IgE content of 50 human sera was calculated from the Z binding assay using the standard curve given in FIG. 3. The sera were obtained from normal and allergic subjects as well as from patients with schistosomiasis. The concentration of IgE was found to range from 100 ng to nearly 50,000 ng per ml of serum; the standard error was less than 5% for each pair of duplicate Z determinations. IgE concentration of each serum was also determined by an I$^{125}$-radio-immunoassay method and by use of the RaShIg-Z conjugate. As shown in FIG. 4, there is good correlation between the two methods over the entire range studied. The regression line fit by least squares to the data in FIG. 4 has a linear correlation coefficient of 0.97.

EXAMPLE 3

Determination of specific anti-ragweed IgE in human serum

Commercial preparation of allergenic extracts of short ragweed pollen were insolubilized to cellulose disks. Specific anti-ragweed IgE antibodies in human sera were assayed in a manner explained diagrammatically in FIG. 2 for total serum IgE, except that ragweed-cellulose disks were used instead of rabbit anti-IgE (RaIgE) disks. Table II shows a comparison between the results obtained with this procedure and those obtained by a commercially available $I^{125}$-radio-allergosorbent test. In all sera tested, there was good correlation between Z enzyme activity and $I^{125}$ bound to the ragweed allergen disks.

TABLE II

| Determination of Specific Anti-ragweed IgE | | |
|---|---|---|
| Serum Sample | Z Bound to Disk | $I^{125}$Bound to Disk |
| 1 | 0 | 0 |
| 2 | 57 | 2100 |
| 3 | 0 | 0 |
| 4 | 6 | 55 |
| 5 | 9 | 84 |
| 6 | 0 | 0 |
| 7 | 25 | 254 |
| 8 | 60 | 1800 |
| 9 | 0 | 0 |

EXAMPLE 4

Conjugation of β-D-Galactosidase to erythrocytes

Sheep erythrocytes were washed three times with PBS and resuspended in PBS to about 15% volume. One ml of the red cell suspension was mixed at 0° C. with 0.1 ml of an enzyme solution containing 40 mg of Z per ml and with 0.1 ml of 3-3'-diaminodipropylamine 0.76 M. One ml of cold 8% glutaraldedhyde was then added to the mixture and the conjugation reaction was allowed to proceed for 1 hour at 0° C. The red cells were spun down, washed four times with cold PBS and finally resuspended in three ml of the same buffer.

The enzyme conjugated to the erythrocytes was measured as described in Example 1 except that the red cells were removed by centrifugation at the end of the incubation with substrate. It was found that a red cell suspension with $2.6 \times 10^8$ cells per ml had an activity of 8469 enzyme units per ml (equivalent to 86000 molecules of enzyme per cell). In contrast, when the sheep erythrocytes were conjugated by the same procedure except that conditioner was omitted, only 41 enzyme units per ml (420 molecules per cell) were obtained. Thus, a 200-fold increase in conjugation efficiency was obtained in the presence of conditioner.

EXAMPLE 5

Use of albumin as conditioner

Rabbit anti-sheep immunoglobulin (RashIg) and β-D-galactosidase (Z) prepared according to Example 1 were dissolved at a concentration of $9 \times 10^{-6}M$ and $6 \times 10^{-6}M$, respectively, in a PBS solution containing $2 \times 10^{-2}M$ glutaraldehyde and $2.2 \times 10^{-4}M$ bovine serum albumin (BSA) as conditioner. The mixture was permitted to react for 60 minutes at room temperature. The reaction was stopped by adding $NaHSO_3$ to $2 \times 10^{-2}M$. The conjugate was isolated and tested as in Example 1. The Z activity of the conjugate prepared with BSA conditioner was more than 7 times that of the corresponding conjugate prepared without conditioner. Furthermore, while the enzymatic activity specifically bound to the immunosorbent disk in the case of conditioned conjugate was 91 times greater than that bound nonspecifically (S/N ratio = 91), the unconditioned conjugate did not bind significantly to either the specific or the non-specific immunosorbent disk (i.e., S/N was indeterminate).

In the same manner, the assay technique of this invention can be used to detect other macromolecules such as hormones and antigens of microorganisms. For these purposes it would be necessary to utilize an appropriate antibody pair instead of the anti-$IgE_1$, and anti-$IgE_2$ shown in FIG. 1. For example, anti-bodies against growth hormone, streptococcal polysaccharide, or tumor specific antigens would be raised in animals of two different species. The antibodies from one species would be coupled to the cellulose disc instead of anti-$IgE_1$, and the antibody from the second species would be substituted for anti-$IgE_2$. Thus, an appropriate "double trap" sandwich may be obtained in each case and the antibodies from the second species would be detected with the low noise, high specificity conditioned enzyme conjugates prepared according to this invention.

What is claimed is:

1. A process for producing an enzyme conjugate with other non-enzyme proteinaceous macromolecules which consists essentially of reacting together an enzyme; a poly-functional coupling agent selected from the group consisting of diisocyanates, carbodiimides, p,p'-di-fluoro-m,m'-dinitrodiphenylsulfone, glutaraldehyde, dimethyladipimate, formaldehyde, bisdiazobenzidine and aromatic halide disulfonates; a polyamine selected from the group consisting of albumin or a diamine selected from a group consisting of phenylenediamine, 4.4'-diaminobenzophenone, p,p'-diaminodiphenyl methane, naphthalene diamine, benzidine, 2,6-diaminopurine, ethylene diamine, propylene diamine diaminodipropylamine and hexamethylene diamine; and a non-enzyme proteinaceous macromolecule selected from the group consisting of antibodies, antigens, allergens and hormones under conditions which preserve enzymatic activity and form said enzyme conjugate.

2. The process of claim 1 wherein the reaction is conducted at ambient temperatures.

3. The process of claim 1 wherein the enzyme is β-D-galactosidase.

4. The process of claim 1 wherein the coupling agent is glutaraldehyde.

5. The process of claim 1 wherein the polyamine is a diamine.

6. The process of claim 1 wherein the polyamine is albumin providing it differs from (the enzyme and) said non-enzyme proteinaceous material.

7. An enzyme conjugate formed by the process of claim 1.

8. The conjugate of claim 8 wherein the enzyme is β-D-galactosidase.

9. The conjugate of claim 7 wherein the polyamine is 3,3'-diaminodipropylamine.

10. The conjugate of claim 7 wherein the polyamine is albumin.

11. The conjugate of claim 7 wherein said macromolecule is an antibody.

12. A process for the detection of antibodies which includes the steps of adhering to a solid support, material which specifically binds antibodies to be detected, adding a body fluid to said adhered material to band antibodies therein to the adhered material, washing the support to remove unbound components of the body fluid, adding the enzyme conjugate of claim 7 to said washed support whereby the conjugate becomes bound to the solid support in proportion to the amount of bound antibodies, washing the support to remove unbound conjugate, and determining the presence of bound antibodies by determining enzymatic activity of said conjugate.

13. The process of claim 12 wherein said material is an allergen.

14. The process of claim 12 wherein IgE antibodies are detected.

15. The process of claim 14 wherein said material is an antibody against IgE.

16. The process of claim 15 which includes the additional step of treating the bound IgE with an antibody against said IgE formed in a different animal species than the antibody of claim 15, and using an enzyme conjugate based upon an antibody of the same animal species as the antibody attached to the solid support.

* * * * *